United States Patent [19]
Vanmaele et al.

[11] Patent Number: 5,455,218
[45] Date of Patent: Oct. 3, 1995

[54] DYE DONOR ELEMENT FOR USE IN A THERMAL DYE TRANSFER PROCESS

[75] Inventors: Luc Vanmaele, Lochristi; Wilhelmus Janssens, Aarschot; Eric Kiekens, Kessel-Lo, all of Belgium

[73] Assignee: Agfa-Gevaert N.V., Mortsel, Belgium

[21] Appl. No.: 372,975

[22] Filed: Jan. 17, 1995

[30] Foreign Application Priority Data

Feb. 28, 1994 [EP] European Pat. Off. ............. 94200500

[51] Int. Cl.⁶ .............................. B41M 5/035; B41M 5/38
[52] U.S. Cl. ................... 503/227; 428/195; 428/913; 428/914
[58] Field of Search ..................... 8/471; 428/195, 428/913, 914; 503/227

[56] References Cited

U.S. PATENT DOCUMENTS

| | | | |
|---|---|---|---|
| 4,910,187 | 3/1990 | Sato et al. | 503/227 |
| 4,973,573 | 11/1990 | Tanaka et al. | 503/227 |
| 5,116,806 | 5/1992 | Vanmaele | 503/227 |

*Primary Examiner*—B. Hamilton Hess
*Attorney, Agent, or Firm*—Brumbaugh, Graves, Donohue & Raymond

[57] ABSTRACT

The present invention provides a dye donor element for use according to the thermal dye transfer process. The dye donor element comprises on a support a dye layer comprising a binder and at least one heterocyclic dye according to formula (I):

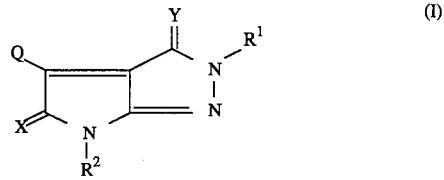

wherein the meanings of the symbols are as defined in the claims and the description.

12 Claims, No Drawings

DYE DONOR ELELMENT FOR USE IN A THERMAL DYE TRANSFER PROCESS

DESCRIPTION

1. Field of the Invention

The present invention relates to novel heterocyclic dyes and to use of these dyes in dye donor elements used in thermal dye transfer methods, in particular thermal dye diffusion or thermal dye sublimation transfer.

2. Background of the Invention

Thermal dye sublimation transfer also called thermal dye diffusion transfer is a recording method in which a dye-donor element provided with a dye layer containing sublimable dyes having heat transferability is brought into contact with a receiver sheet and selectively, in accordance with a pattern information signal, is heated by means of a thermal printing head provided with a plurality of juxtaposed heat-generating resistors, so that dye is transferred from the selectively heated regions of the dye-donor element to the receiver sheet and forms a pattern thereon, the shape and density of which is in accordance with the pattern and intensity of heat applied to the dye-donor element.

A dye-donor element for use according to thermal dye sublimation transfer usually comprises a very thin support e.g. a polyester support, one side of which has been covered with a dye layer comprising the printing dyes. Usually, an adhesive or subbing layer is provided between the support and the dye layer. Normally, the opposite side of the support is covered with a slipping layer that provides a lubricated surface against which the thermal printing head can pass without suffering abrasion. An adhesive layer may be provided between the support and the slipping layer.

A dye-image receiving element for use according to thermal dye sublimation transfer usually comprises a support, e.g. paper or a transparant film coated with a dye-image receiving layer, into which the dye can diffuse more readily. An adhesive layer may be provided between the support and the receiving layer. A releasing agent may be contained in the receiving layer or in a separate layer on top of said receiving layer to improve the releasability of the receiving element from the donor element after the dye transfer has been effected.

The dye layer can be a monochromic dye layer or it may comprise sequential repeating areas of differently coloured dyes e.g. dyes having a cyan, magenta, yellow, and optionally black-colour hue. When a dye-donor element containing three or more primary colour dye areas is used, a multicolour image can be obtained by sequentially performing the dye transfer process steps for each colour area.

Black-coloured images can be obtained by thermal dye sublimation transfer printing either by sequentially performing the dye transfer process steps for the three primary colours cyan, magenta, and yellow by means of a dye-donor element comprising sequential repeating areas of cyan, magenta, and yellow coloured dyes or by performing only one transfer step by means of a dye-donor element having a black-coloured dye layer containing a mixture of yellow, magenta, and cyan coloured image dyes. The latter of these two methods is preferred because of i.a. the ease of manufacturing the donor element containing only one dye area, less time-consuming recording with only one transfer step, and avoiding the problem of transfer in register of the respective dyes in the respective dye areas. Mixtures of yellow, magenta, and cyan dyes for forming a black-coloured dye layer of such a black-coloured dye-donor element have been described in e.g. European patent application No. 92202157.1, EP 453,020, U.S. Pat. No. 4,816,435, and JP 01/136,787.

An important application of the recording of monochromic black images by thermal dye sublimation transfer is the recording on transparant film receiver of hard copies of medical diagnostic images formed by e.g. ultrasound techniques. Such a hard copy is considered to be an ecologically more acceptable and more convenient substitute for the black-and-white silver hard copy formed by development of conventional photographic silver halide film materials where processing solutions comprising silver salt residues have to be treated carefully before disposal.

In order to obtain an image close to images obtained with conventional photographic silver halide materials the black-coloured mixture of organic dyes used in thermal dye sublimation transfer printing should behave optically as black silver.

In the medical world physicians and radiologists evaluate X-ray photographs or other images on a light box or negatoscope. These light boxes contain fluorescent lamps as light source. The spectral emission of fluorescent lamps depends on the phosphors used in the fluorescent lamp, said phosphors having peak emissions. As a result, fluorescent lamps do not show a continuous emission spectrum. Furthermore, there is no standardization in the type of fluorescent lamp used in said negatoscopes.

There is not so much a problem when viewing classical medical images composed of silver metal on the light boxes, since the spectral absorption characteristics of silver are constant over the whole visible spectrum. The hue of the silver image does not change whatever the spectral properties of the light source are, by which the image is being viewed.

However, when the black image is composed of coloured dyes, problems of hue changes may arise, because the spectral absorption characteristics of organic dyes are not constant over the whole range of the visible spectrum. A black-coloured dye mixture having a neutral look when viewed with one light source will not have a neutral look when viewed with a spectrally different light source. This phenomenon of hue change of an image when viewed with a different light source is highly unwanted, especially when medical diagnostic images have to be evaluated.

The characteristics of colour dyes that can be used for composing black-coloured dye mixtures have been further described in EP-A 453020.

Many of the dyes proposed so far for use in thermal dye sublimation transfer are not sufficient in performance since they yield inadequate transfer densities at reasonable coating coverages, or because they have inadequate spectral characteristics for substractive colour systems, or because they have a poor lightfastness.

As mentioned before, for forming a black record by thermal dye sublimation transfer the transfer currently has been performed by means of a dye-donor element having a black-coloured layer containing a mixture of yellow, magenta, and cyan coloured dyes.

However, the conventional materials are insufficient in performance in that the density of the transferred black image obtained therefrom is too low, especially when transfer has been performed onto a transparent dye-image receiving element.

To fulfil the above described requirements for black-coloured dye mixtures, it would be an advantage that the colour dyes have a high molar extinction coefficient at the absorption maximum combined with high side absorptions. As a consequence, fewer dyes and/or smaller amounts of dyes would be needed to reach higher black density values, which would also result in less overloading of the polymer matrix of the dye donor layer.

SUMMARY OF THE INVENTION

It is therefore an object of the present invention to provide novel heterocyclic dyes that are thermally transferable and that have a high molar extinction coefficient, preferably in combination with substantial side absorption i.e. the heterocyclic dyes preferably exhibit a broad absorption in the visual part of the spectrum.

It is a further object of the present invention to provide dye donor elements, in particular magenta and black dye donor elements yielding transferred dye images having a high density and good light stability.

Still a further object of the present invention is to provide a method for making high density magenta or black dye images having a good light stability.

Further objects of the present invention will become clear from the description hereinafter.

In accordance with the present invention there is provided a dye donor element for use according to the thermal dye transfer process, said dye donor element comprising on a support a dye layer comprising a binder and at least one heterocyclic dye according to formula (I):

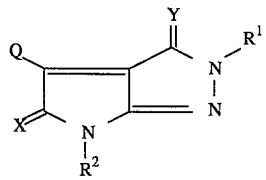

(I)

wherein:

X and Y each independently represents S or O;

Q represents an aromatic ring including a hetero-aromatic ring;

$R^1$ and $R^2$ each independently represents hydrogen, an alkyl group, an alkenyl group, an alkynyl group, an aryl group, a heterocyclic ring, a nitrile, a formyl group, a ketone, an acetal, a thioaldehyde, a thioketone, a thioacetal, an amide, an oxycarbonyl group, an oxythiocarbonyl group, a thiocarbonyl group, a thioxycarbonyl group, a thio-amide, an aminal group, an 1,3-oxathiolan, a thioxythiocarbonyl group, an acylamino group, a thiocarbonamido group, an amino group, a hydroxy, an alkoxy, a thiol, an alkylthio, an aminosulphonyl, a sulphonyl or a phosphonate group.

According to the present invention there is further provided a method for making an image comprising the steps of:

bringing the dye layer of a dye donor element as defined above in face-to-face relationship with a receiving layer of an image receiving element;

image-wise heating a thus obtained assemblage thereby forming a transfer image on said receiving element and separating said dye donor element from said image receiving element.

DETAILED DESCRIPTION OF THE INVENTION

The dyes according to formula (I) above can be prepared according to the methods known to those skilled in the art of organic synthesis or they can be prepared similar to the method of preparation of dye C8 (table 1). Dye C8 was prepared according to scheme 1 below.

Preparation of dye C8 of table 1:

Step 1:

109 ml of triethylamine is added to a solution of 137 g of N-butyl,N-sec.-butylaniline in 600 ml of dichloromethane at 0° C. 69 ml of oxalyl chloride are slowly added at −5° C. while keeping the temperature below 2° C. The solution is stirred for 2.5 hours. 180 ml of ethanol are added while maintaining the temperature below 20° C. The solution is poured into water and the organic layer is washed with a sodium bicarbonate solution and a saturated sodium chloride solution. The solvent is removed under reduced pressure and compound A is purified by column chromatography (eluent: dichloromethane). 86 g of compound A are obtained.

Step 2:

A mixture of 40 g of compound A, 30 g of 1-phenyl-3-amino-5-pyrazolone and 45 g of zinc chloride in 400 ml of 1-methoxy-2-propanol is refluxed for two hours. The solution is filtered warm; the filtrate is poured into 1 l of methanol. The precipitate is filtered and washed with methanol. After drying 32 g of compound B are obtained.

Step 3:

3.1 g of methylglycol benzenesulphonate is added to a suspension of 2.4 g of potassium iodide in 30 ml of N,N-dimethylacetamide (hereinafter abbreviated as DMA) at 70° C. The reaction mixture is heated at 70° C. for 4 hours (solution 1).

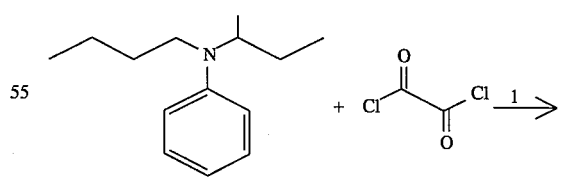

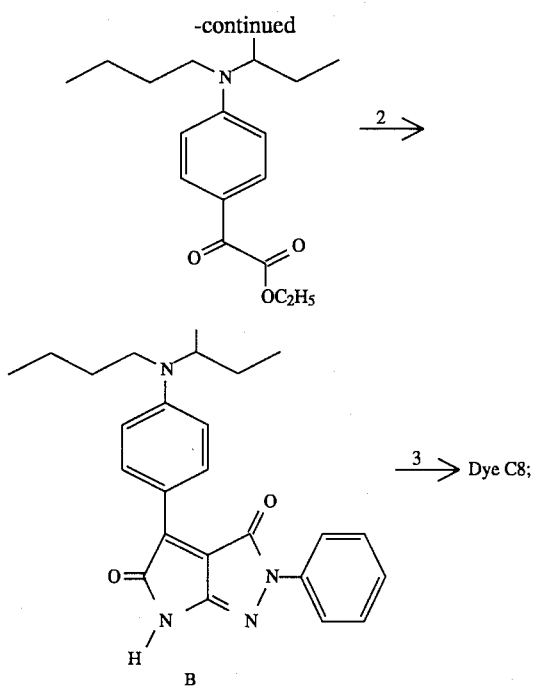

0.5 g of sodium hydroxide is added to a solution of 3 g of compound B in 20 ml DMA. The solution (solution 2) is stirred for 20 minutes. Solution 2 is added to solution 1 and stirred for 30 minutes at 70° C. The solution is poured into 400 ml of water and extracted with ethyl acetate. The organic layer is washed with water, dried on sodium sulphate and concentrated under reduced pressure. The residue is purified by column chromatography (dichloromethane/ethyl acetate; 98/2) to obtain 1.6 g of pure compound C8 (mp. 104° C.).

According to a preferred embodiment of the present invention the aromatic group Q of general formula (I) corresponds to the following formula (II):

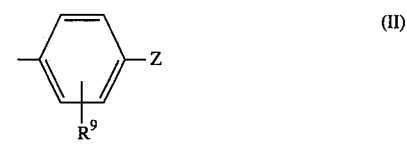

(II)

wherein Z represents an amine, an alkoxy group, an alkylthio group and $R^9$ represents hydrogen, an alkyl, an aryl, a heterocyclic ring, an alkoxy, an aryloxy, an alkylthio an amine, an acylamino, an amide, a nitro, a nitrile or a halogen.

Examples of dyes according to the present invention are listed in table 1.

TABLE 1

| Dye | $R^1$ | $R^2$ | $R^3$ |
|---|---|---|---|
| C1 | $CH_3$ | $CH_3$ | $C_4H_9$ |
| C2 | $CH_3$ | $CH_3$ | $CH(CH_3)C_2H_5$ |
| C3 | $C_4H_9$ | $CH(CH_3)C_2H_5$ | H |
| C4 | $C_4H_9$ | $CH(CH_3)C_2H_5$ | $CH_3$ |
| C5 | $C_4H_9$ | $CH(CH_3)C_2H_5$ | $C_4H_9$ |
| C6 | $C_4H_9$ | $CH(CH_3)C_2H_5$ | $CH(CH_3)C_2H_5$ |
| C7 | $C_4H_9$ | $CH(CH_3)C_2H_5$ | $CH_2CH(CH_3)_2$ |
| C8 | $C_4H_9$ | $CH(CH_3)C_2H_5$ | $CH_2CH_2OCH_3$ |
| C9 | $C_4H_9$ | $CH(CH_3)C_2H_5$ | $CH(CH_3)CH_2OCH_3$ |
| C10 | $CH_3$ | $CH_3$ | $CH_3$ |
| C11 | $C_4H_9$ | $CH(CH_3)C_2H_5$ | $COCH_3$ |
| C12 | $C_2H_5$ | $C_2H_5$ | $C_3H_7$ |
| C13 | $C_2H_5$ | $C_2H_5$ | $CH(CH_3)_2$ |
| C14 | $C_4H_9$ | $C_4H_9$ | $SO_2CH_3$ |
| C15 | $C_4H_9$ | $C_4H_9$ | $SO_2CH_3$ |
| C16 | $C_2H_4OH$ | $C_2H_5$ | $C_4H_9$ |
| C17 | $C_2H_4CN$ | $C_2H_4CN$ | $C_4H_9$ |
| C18 | $C_2H_4OCOCH_3$ | $C_2H_5$ | $C_4H_9$ |
| C19 | $C_4H_9$ | $CH(CH_3)C_2H_5$ | $COCH_2OCH_3$ |
| C20 | $C_4H_9$ | $CH(CH_3)C_2H_5$ | $COCOOC_2H_5$ |
| C21 | $C_4H_9$ | $CH(CH_3)C_2H_5$ | $COCON(C_2H_5)_2$ |

TABLE 1-continued
| Dye | R¹ | R² | R³ |
|---|---|---|---|
C22
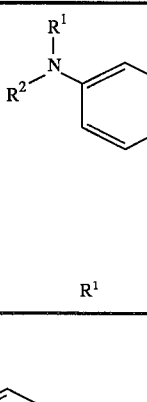
C23
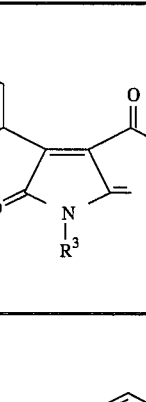
C24
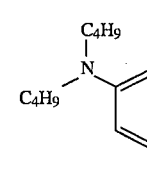
C25
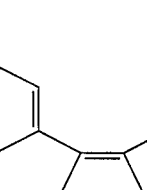
C26
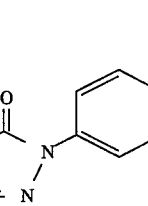

TABLE 1-continued

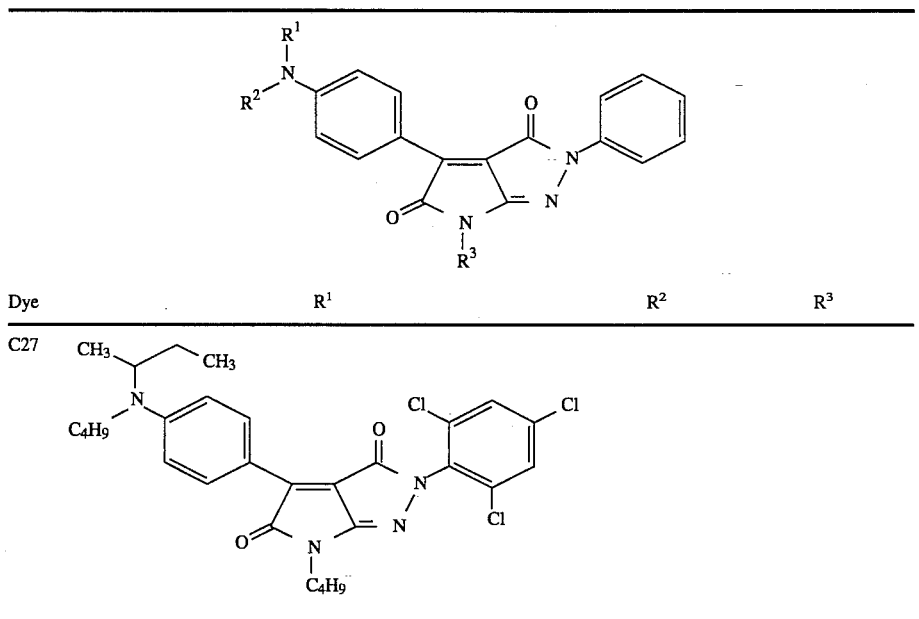

| Dye | R¹ | R² | R³ |
| --- | --- | --- | --- |
| C27 | CH₃CH(CH₃)- (isopropyl shown with N) | C₄H₉ | C₄H₉; N-aryl = 2,4,6-trichlorophenyl |

The dyes in accordance with the present invention can be used as filter dyes e.g. for silver halide colour photographic materials and also as antihalation dyes. They can be used in inkjet printing, resistive ribbon printing, in inks e.g. for laser applications, in textile, in lacquers, and in paints. They can also be used for transfer printing on fabrics.

According to a preferred embodiment of the present invention the dyes are used in the dye layer of a dye-donor element for thermal dye sublimation transfer.

The dye layer of the dye-donor element is formed preferably by adding the dyes, a polymeric binder medium, and other optional components to a suitable solvent or solvent mixture, dissolving or dispersing by ball-milling these ingredients to form a coating composition that is applied to a support, which may have been provided first with an adhesive or subbing layer, and dried.

The dye layer thus formed has a thickness of about 0.2 to 5.0 μm, preferably 0.4 to 2.0 μm, and the amount ratio of dye to binder ranges from 9:1 to 1:3 by weight, preferably from 2:1 to 1:2 by weight.

The following polymers can be used as polymeric binder: cellulose derivatives, such as ethyl cellulose, hydroxyethyl cellulose, ethylhydroxy cellulose, ethylhydroxyethyl cellulose, hydroxypropyl cellulose, methyl cellulose, cellulose nitrate, cellulose acetate formate, cellulose acetate hydrogen phthalate, cellulose acetate, cellulose acetate propionate, cellulose acetate butyrate, cellulose acetate pentanoate, cellulose acetate benzoate, cellulose triacetate; vinyl-type resins and derivatives, such as polyvinyl alcohol, polyvinyl acetate, polyvinyl butyral, copolyvinyl butyral-vinyl acetal-vinyl alcohol, polyvinyl pyrrolidone, polyvinyl acetoacetal, polyacrylamide; polymers and copolymers derived from acrylates and acrylate derivatives, such as polyacrylic acid, polymethyl methacrylate and styrene-acrylate copolymers; polyester resins; polycarbonates; Poly(styrene-co-acrylonitrile); polysulfones; polyphenylene oxide; organosilicones such as poly-siloxanes; epoxy resins and natural resins, such as gum arabic. Preferably, the binder for the dye layer of the present invention comprises cellulose acetate butyrate or poly(styrene-co-acrylonitrile).

The dye layer of a dye donor element in connection with the present invention may be a continuous dye layer of one or more dyes or the dye layer may consist of a repeating sequence of at least two dye frames. According to a particular embodiment for making colour images the dye donor element can consist of a repeating sequence of a yellow, magenta and cyan dye frame.

The dyes of the present invention can be used alone or mixed with one another, or even mixed with other colour dyes.

The dyes according to formula (I) are particularly useful for making black and white images using the thermal transfer process. Such black and white images may be composed of 3 primary dyes, i.e. yellow, magenta and cyan, that are transferred in sequence to an image receiving element or said black and white images may be obtained by transferring a black mixture of several dyes. In each case at least one of the constituting dyes will be a dye according to formule (I).

Typical and specific examples of other primary colour dyes for use in thermal dye sublimation transfer have been described in e.g. EP 400,706, EP 209,990, EP 216,483, EP 218,397, EP 227,095, EP 227,096, EP 229,374, EP 235,939, EP 247,737, EP 257,577, EP 257,580, EP 258,856, EP 279,330, EP 279,467, EP 285,665, U.S. Pat. Nos. 4,743,582, 4,753,922, 4,753,923, 5,026,677, 4,757,046, 4,769,360, 4,771,035, JP 84/78,894, JP 84/78,895, JP 84/78,896, JP 84/227,490, JP 84/227,948, JP 85/27,594, JP 85/30,391, JP 85/229,787, JP 85/229,789, JP 85/229,790, JP 85/229,791, JP 85/229,792, JP 85/229,793, JP 85/229,795, JP 86/268, 493, JP 86/268,494, JP 85/268,495, and JP 86/284,489.

The coating layer may also contain other additives, such as curing agents, preservatives, organic or inorganic fine particles, dispersing agents, antistatic agents, defoaming agents, viscosity-controlling agents, these and other ingredients having been described more fully in EP 133,011, EP 133,012, EP 111,004, and EP 279,467.

Any material can be used as the support for the dye-donor element provided it is dimensionally stable and capable of withstanding the temperatures involved, up to 400° C. over a period of up to 20 msec, and is yet thin enough to transmit heat applied on one side through to the dye on the other side to effect transfer to the receiver sheet within such short periods, typically from 1 to 10 msec. Such materials include polyesters such as polyethylene terephthalate, polyamides, polyacrylates, polycarbonates, cellulose esters, fluorinated polymers, polyethers, polyacetals, polyolefins, polyimides, glassine paper and condenser paper. Preference is given to a support comprising polyethylene terephthalate. In general, the support has a thickness of 2 to 30 μm. The support may also be coated with an adhesive of subbing layer, if desired.

The dye layer of the dye-donor element can be coated on the support or printed thereon by a printing technique such as a gravure process.

A dye-barrier layer comprising a hydrophilic polymer may also be employed between the support and the dye layer of the dye-donor element to enhance the dye transfer densities by preventing wrong-way transfer of dye backwards to the support. The dye barrier layer may contain any hydrophilic material that is useful for the intended purpose. In general, good results have been obtained with gelatin, polyacrylamide, polyisopropyl acrylamide, butyl methacrylate-grafted gelatin, ethyl methacrylate-grafted gelatin, ethyl acrylate-grafted gelatin, cellulose monoacetate, methylcellulose, polyvinyl alcohol, polyethyleneimine, polyacrylic acid, a mixture of polyvinyl alcohol and polyvinyl acetate, a mixture of polyvinyl alcohol and polyacrylic acid, or a mixture of cellulose monoacetate and polyacrylic acid. Suitable dye barrier layers have been described in e.g. EP 227,091 and EP 228,065. Certain hydrophilic polymers e.g. those described in EP 227,091 also have an adequate adhesion to the support and the dye layer, so that the need for a separate adhesive or subbing layer is avoided. These particular hydrophilic polymers used in a single layer in the dye-donor element thus perform a dual function, hence are referred to as dye-barrier/subbing layers.

Preferably the reverse side of the dye-donor element has been coated with a slipping layer to prevent the printing head from sticking to the dye-donor element. Such a slipping layer would comprise a lubricating material such as a surface-active agent, a liquid lubricant, a solid lubricant or mixtures thereof, with or without a polymeric binder. The surface-active agents may be any agents known in the art such as carboxylates, sulfonates, phosphates, aliphatic amine salts, aliphatic quaternary ammonium salts, polyoxyethylene alkyl ethers, polyethylene glycol fatty acid esters, fluoroalkyl $C_2$–$C_{20}$ aliphatic acids. Examples of liquid lubricants include silicone oils, synthetic oils, saturated hydrocarbons, and glycols. Examples of solid lubricants include various higher alcohols such as stearyl alcohol, fatty acids and fatty acid exters. Suitable slipping layers have been described in e.g. EP 138,483, EP 227,090, U.S. Pat. Nos. 4,567,113, 4,572,860, 4,717,711. Preferably the slipping layer comprises a styrene-acrylonitrile copolymer or a styrene-acrylonitrile-butadiene copolymer or a mixture thereof or a polycarbonate as described in European patent application no. 91202071.6, as binder and a polysiloxane-polyether copolymer or polytetrafluoroethylene or a mixture thereof as lubricant in an amount of 0.1 to 10% by weight of the binder or binder mixture.

The support for the receiver sheet that is used with the dye-donor element may be a transparent film of e.g. polyethylene terephthalate, a polyether sulfone, a polyimide, a cellulose ester or a polyvinyl alcohol-co-acetal. The support may also be a reflective one such as a baryta-coated paper, polyethylene-coated paper or white polyester i.e. white-pigmented polyester. Blue-coloured polyethylene terephthalate film can also be used as support.

To avoid poor adsorption of the transferred dye to the support of the receiver sheet this support must be coated with a special layer called dye-image-receiving layer, into which the dye can diffuse more readily. The dye-image-receiving layer may comprise e.g. a polycarbonate, a polyurethane, a polyester, a polyamide, polyvinyl chloride, polystyrene-co-arcylonitrile, polycaprotactone, or mixtures thereof. The dye-image receiving layer may also comprise a heat-cured product of poly(vinyl chloride/co-vinyl acetate/co-vinyl alcohol) and polyisocyanate. Suitable dye-image receiving layers have been described in e.g. EP 133,011, EP 133,012, EP 144,247, EP 227,094, and EP 228,066.

In order to improve the light-fastness and other stabilities of recorded images UV-absorbers, singlet oxygen quenchers such as HALS-compounds (Hindered Amine Light Stabilizers) and/or antioxidants can be incorporated into the dye-image-receiving layer.

The dye layer of the dye-donor element or the dye-image-receiving layer of the receiver sheet may also contain a releasing agent that aids in separating the dye-donor element from the receiver sheet after transfer. The releasing agents can also be incorporated in a separate layer on at least part of the dye layer and/or of the dye-image-receiving layer. Suitable releasing agents are solid waxes, fluorine- or phosphate-containing surface-active agents and silicone oils. Suitable releasing agents have been described in e.g. EP 133,012, JP 85/19,138, and EP 227,092.

The dye-donor elements according to the invention are used to form a dye transfer image, which process comprises placing the dye layer of the dye-donor element in face-to-face relation with the dye-image-receiving layer of the receiver sheet and image-wise heating from the back of the dye-donor element. The transfer of the dye is accomplished by heating for about several milliseconds at a temperature of 400° C.

When the process is performed for but one single colour, a monochromic dye transfer image is obtained. A multicolour image can be obtained by using a dye-donor element containing three or more primary colour dyes and sequentially performing the process steps described above for each colour. The above sandwich of dye-donor element and receiver sheet is formed on three occasions during the time when heat is applied by the thermal printing head. After the first dye has been transferred, the elements are peeled apart. A second dye-donor element (or another area of the dye-donor element with a different dye area) is then brought in register with the dye-receiving element and the process is repeated. The third colour and optionally further colours are obtained in the same manner.

In addition to thermal heads, laser light, infrared flash, or heated pens can be used as the heat source for supplying heat energy. Thermal printing heads that can be used to transfer dye from the dye-donor elements of the present invention to a receiver sheet are commercially available. In case laser light is used, the dye layer or another layer of the dye element has to contain a compound that absorbs the light emitted by the laser and converts it into heat e.g. carbon black.

Alternatively, the support of the dye-donor element may be an electrically resistive ribbon consisting of e.g. a multilayer structure of a carbon-loaded polycarbonate coated with a thin aluminium film. Current is injected into the resistive ribbon by electrically addressing a printing head electrode resulting in highly localized heating of the ribbon beneath the relevant electrode. The fact that in this case the heat is generated directly in the resistive ribbon and that it is thus the ribbon that gets hot leads to an inherent advantage in printing speed using the resistive ribbon/electrode head technology as compared to the thermal head technology, according to which the various elements of the thermal head get hot and must cool down before the head can move to the next printing position.

The following examples illustrate the invention in more detail without, however, limiting the scope thereof. All parts are by weight unless otherwise specified.

EXAMPLE 1

The absorption maxima ($\lambda_{max}$) of the dyes identified below were determined in methanol. The solubility (A) was determined in 2-butanone at room temperature. The results are listed in Table 2.

| Dye | $\lambda_{max}$ | $\epsilon_{max}$ | A (%) |
|---|---|---|---|
| C1 (a) | 556 | 38290 | 1.5 |
| C2 (a) | 556 | 42104 | 1.0 |
| C3 (a) | 566 | 45537 | 1.0 |
| C4 | 570 | 43501 | 2.0 |
| C5 | 572 | 46033 | 10.0 |
| C6 | 570 | 45793 | 10.0 |
| C7 | 572 | 47353 | 10.0 |
| C8 | 572 | 45597 | 8.0 |
| C9 | 572 | 45674 | 20.0 |
| C10 (b) | 562 | 39362 | <0.1 |
| C11 | 526 | 32470 | 2.0 |

(a) determined in dichloromethane/methanol (1:9)
(b) determined in N,N-dimethylacetamide

EXAMPLE 2

Receiver sheets were prepared by coating a subbed polyethylene terephthalate film having a thickness of 175 μm with a dye-image-receiving layer from a solution in ethyl methyl ketone of 3.6 g/m² of poly(vinyl chloride/co-vinyl acetate/co-vinyl alcohol) (Vinylite VAGD supplied by Union Carbide), 0.336 g/m² of polyisocyanate (Desmodur VL supplied by Bayer AG), and 0.2 g/m² of hydroxy-modified polydimethylsiloxane (Tegomer H SI 2111 supplied by Goldschmidt).

Dye-donor elements for use according to thermal dye sublimation transfer were prepared as follows.

A solution in methyl ethyl ketone of 0.5% by weight of dye and 0.5% by weight of poly(styrene-co-acrylonitrile) (PSA) (Luran 388S, supplied by BASF Germany) as a binder was prepared.

A dye layer having a wet thickness of 100 μm was coated from this solution on a polyethylene terephthalate film support having a thickness of 6 μm and carrying a conventional subbing layer. The resulting dye layer was dried by evaporation of the solvent.

The opposite side of the film support was coated with a subbing layer of a copolyester comprising ethylene glycol, adipic acid, neopentyl glycol, terephthalic acid, isophthalic acid, and glycerol.

The resulting subbing layer was covered with a solution in methyl ethyl ketone of 0.5 g/m² of a polycarbonate having the following structural formula to form a heat-resistant layer:

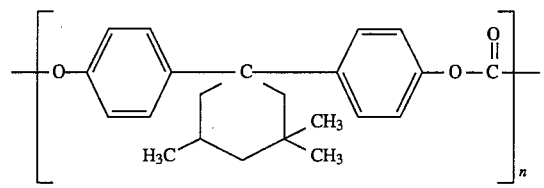

wherein n has a value giving a polycarbonate with a relative viscosity of 1.295 (measured in a 0.5% by weight solution in dichloromethane).

Finally, a top layer of polyether-modified polydimethylsiloxane (Tegoglide 410, Goldschmidt) was coated from a solution in isopropanol on the resulting heat-resistant polycarbonate layer.

The dye-donor element was printed in combination with a receiver sheet in a Mitsubishi colour video printer CP100E.

The receiver sheet was separated from the dye-donor element and the colour density value of the recorded image was measured in reflex (with a white paper behind the transparent receiver sheet) by means of a Macbeth TR 924 densitometer in the red, green, and blue regions in Status A mode.

The above described experiment was repeated for each of the dyes identified in table 3 hereinafter. The results are also given in table 3.

TABLE 3

| Dye | $D_{max}$ | Spectral absorption in Status A behind filter: | | |
|---|---|---|---|---|
| | | Red | Green | Blue |
| C1 | 279 | 53 | 150 | 31 |
| C2 | 244 | 50 | 150 | 31 |
| C3 | 203 | 117 | 150 | 27 |
| C4 | 213 | 105 | 150 | 28 |
| C5 | 201 | 95 | 150 | 27 |
| C6 | 205 | 89 | 150 | 27 |
| C7 | 198 | 94 | 150 | 27 |
| C8 | 212 | 106 | 150 | 27 |
| C9 | 186 | 100 | 150 | 18 |

In the following table 4 the structural formulae and side absorptions of commercially available magenta colour dyes CM1 to CM4 are given for comparison with the side absorptions of the dyes according to the present invention.

TABLE 4

| Dye formula | Spectral absorption in Status A behind filter | | |
|---|---|---|---|
| | Red | Green | Blue |
| (isothiazole azo dye with N-ethyl-N-benzyl amino and NHCOCH3 substituents) | 17 | 150 | 47 |
| (1,4-dihydroxy-2-phenoxy anthraquinone) | 8 | 150 | 57 |
| (isothiazole azo dye with N-ethyl-N-(CH2)2-OCO-CH3 amino and CH3 substituents) | 13 | 150 | 45 |
| (dicyanovinyl compound with N-butyl-N-(CH2)2-phenyl amino) | 9 | 150 | 34 |

EXAMPLE 3

Receiver sheets were prepared as described in example 2. Black dye donor elements were prepared as follows: The amounts of dyes as indicated in the following table 5 were added each time to 10 ml of a solution of 0.5% by weight of poly(styrene-co-acrylonitrile) (Luran 388S, supplied by BASF Germany) in ethyl methyl ketone. The resulting black coloured dye mixtures were coated, printed, and evaluated as described in the above Example 2, the maximum densities being measured in transmission.

The results of the tests are listed in the following table 5. The prior art dyes C-cyan, C-yellow 1 and C-yellow 2 having the following structural formulae were used for comparison in the tests.

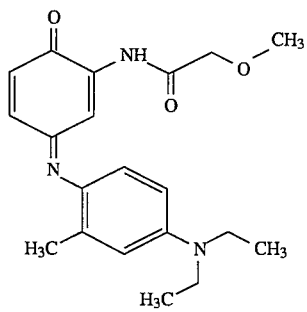

C-Cyan

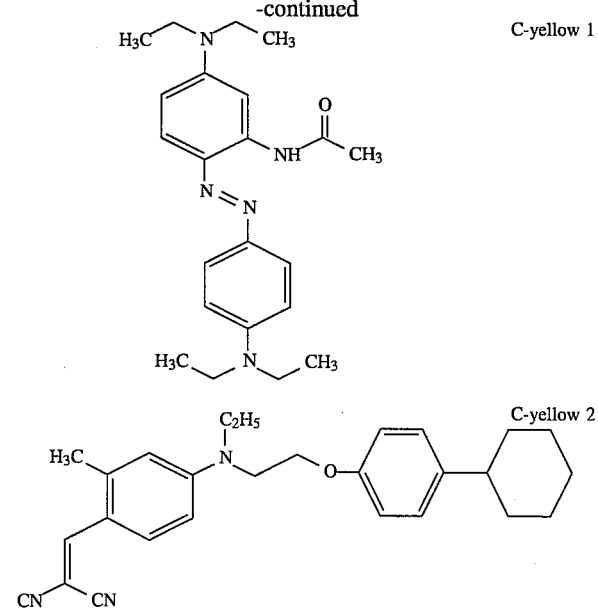

C-yellow 1

C-yellow 2

The above dyes can be prepared as described or indicated in U.S. Pat. No. 5,169,828 and the corresponding EP 453.020.

TABLE 5

| Test No. | Dye | Amount of dye in mg | Spectral absorption in Status A behind filter | | | |
|---|---|---|---|---|---|---|
| | | | Red | Green | Blue | Vis. |
| 1 | C-cyan | 28 | | | | |
| | C1 | 44 | 128 | 177 | 163 | 159 |
| | C-yellow 1 | 12 | | | | |
| | C-yellow 2 | 25 | | | | |
| 2 | C-cyan | 28 | | | | |
| | C2 | 44 | 122 | 185 | 154 | 161 |
| | C-yellow 1 | 13 | | | | |
| | C-yellow 2 | 25 | | | | |
| 3 | C-cyan | 28 | | | | |
| | C4 | 44 | 129 | 129 | 121 | 135 |
| | C-yellow 1 | 13 | | | | |
| | C-yellow 2 | 25 | | | | |
| 4 | C-cyan | 28 | | | | |
| | C5 | 44 | 147 | 147 | 148 | 153 |
| | C-yellow 1 | 13 | | | | |
| | C-yellow 2 | 25 | | | | |
| 5 | C-cyan | 28 | | | | |
| | C6 | 44 | 151 | 157 | 154 | 161 |
| | C-yellow 1 | 13 | | | | |
| | C-yellow 2 | 25 | | | | |
| 6 | C-cyan | 28 | | | | |
| | C7 | 44 | 157 | 161 | 154 | 169 |
| | C-yellow 1 | 13 | | | | |
| | C-yellow 2 | 25 | | | | |
| 7 | C-cyan | 28 | | | | |
| | C8 | 44 | 141 | 133 | 137 | 141 |
| | C-yellow 1 | 13 | | | | |
| | C-yellow 2 | 25 | | | | |
| 8 | C-cyan | 23 | | | | |
| | C9 | 38 | 104 | 124 | 163 | 123 |
| | C-yellow 1 | 18 | | | | |
| | C-yellow 2 | 31 | | | | |

The results listed in Table 5 show that by means of dye-donor elements incorporating a dye mixture comprising a heterocyclic dye according to the present invention transferred dye images can be made, which may have extremely neutral, high density black values.

We claim:

1. A dye donor element for use according to the thermal dye transfer process, said dye donor element comprising on a support a dye layer comprising a binder and at least one heterocyclic dye according to formula (I):

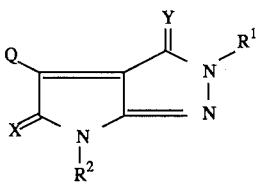

(I)

wherein:

X and Y each independently represents S or O;

Q represents an aromatic ring;

R$^1$ and R$^2$ each independently represents hydrogen, an alkyl group, an alkenyl group, an alkynyl group, an aryl group, a heterocyclic ring, a nitrile, a formyl group, a ketone, an acetal, a thioaldehyde, a thioketone, a thioacetal, an amide, an oxycarbonyl group, an oxythiocarbonyl group, a thiocarbonyl group, a thioxycarbonyl group, a thio-amide, an aminal group, an 1,3-oxathiolan, a thioxythiocarbonyl group, an acylamino group, a thiocarbonamido group, an amino group, a hydroxy, an alkoxy, a thiol, an alkylthio, an aminosulphonyl, a sulphonyl or a phosphonate group.

2. A dye donor element according to claim 1 wherein said dye layer consists of a repeating sequence of at least two dye frames, at least one of said dye frames containing a dye according to formula (I).

3. A dye donor element according to claim 2 wherein said dye layer consists of a repeating sequence of a yellow, magenta and cyan coloured dye frame.

4. A dye donor element according to claim 1 wherein said dye layer comprises a black mixture of dyes.

5. A dye donor element according to claim 1 wherein said aromatic ring Q corresponds to the following formula (II):

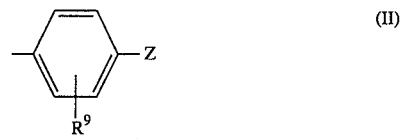

(II)

wherein Z represents an amine, an alkoxy group, an alkylthio group and R$^9$ represents hydrogen, an alkyl, an aryl, a heterocyclic ring, an alkoxy, an aryloxy, an alkylthio, an amine, an acylamino, an amide, a nitro, a nitrile or a halogen.

6. A dye donor element according to claim 1 wherein Q represents a hetero-aromatic ring.

7. A method for making an image comprising the steps of: bringing the dye layer of a dye donor element comprising on a support a dye layer comprising a binder and at least one heterocyclic dye according to formula (I):

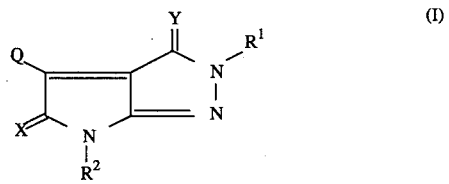

(I)

wherein:

X and Y each independently represents S or O;

Q represents an aromatic ring;

R$^1$ and R$^2$ each independently represents hydrogen, an alkyl group, an alkenyl group, an alkynyl group, an aryl group, a heterocyclic ring, a nitrile, a formyl group, a ketone, an acetal, a thioaldehyde, a thioketone, a thioacetal, an amide, an oxycarbonyl group, an oxythiocarbonyl group, a thiocarbonyl group, a thioxycarbonyl group, a thio-amide, an aminal group, an 1,3-oxathiolan, a thioxythiocarbonyl group, an acylamino group, a thiocarbonamido group, an amino group, a hydroxy, an alkoxy, a thiol, an alkylthio, an aminosulphonyl, a sulphonyl or a phosphonate group in face-to-face relationship with a receiving layer of an image receiving element;

image-wise heating a thus obtained assemblage thereby forming a transfer image on said receiving element and separating said dye donor element from said image receiving element.

8. A method according to claim 7 wherein said dye layer consists of a repeating sequence of at least two dye frames, at least one of said dye frames containing a dye according to formula (I).

9. A method according to claim 8 wherein said dye layer consists of a repeating sequence of a yellow, magenta and cyan coloured dye frame.

10. A method according to claim 7 wherein said dye layer comprises a black mixture of dyes.

11. A method according to claim 7 wherein said aromatic ring Q corresponds to the following formula (II):

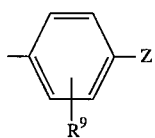 (II)
wherein Z represents an amine, an alkoxy group, an alkylthio group and $R^9$ represents hydrogen, an alkyl, an aryl, a heterocyclic ring, an alkoxy, an aryloxy, an alkylthio, an amine, an acylamino, an amide, a nitro, a nitrile or a halogen.
12. A method according to claim 7 wherein Q represents a heteroaromatic ring.
* * * * *

UNITED STATES PATENT AND TRADEMARK OFFICE
CERTIFICATE OF CORRECTION

PATENT NO. : 5,455,218　　　　　　　　　　　　　　Page 1 of 2
DATED : October 3, 1995
INVENTOR(S) : Vanmaele et al.

It is certified that error appears in the above-indentified patent and that said Letters Patent is hereby corrected as shown below:

<u>Column 4, between lines 43-44 (above "Step 3")</u>, insert --Scheme 1--;

<u>Column 7,</u>

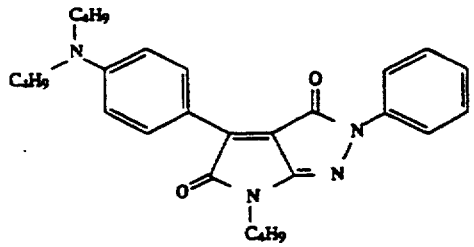

should read

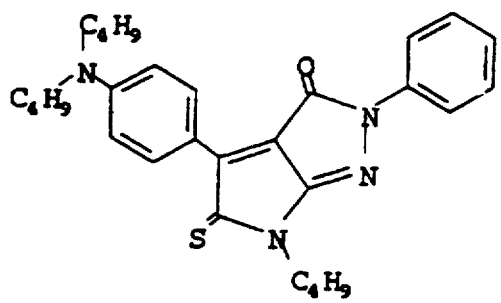

UNITED STATES PATENT AND TRADEMARK OFFICE
CERTIFICATE OF CORRECTION

PATENT NO. : 5,455,218

DATED : October 3, 1995

INVENTOR(S) : Vanmaele et al.

It is certified that error appears in the above-indentified patent and that said Letters Patent is hereby corrected as shown below:

Column 9, line 60, "Poly" should read --poly--.

Signed and Sealed this

Twentieth Day of February, 1996

Attest:

BRUCE LEHMAN

Attesting Officer

Commissioner of Patents and Trademarks